US00PP31613P2

(12) United States Plant Patent
Hofmann

(10) Patent No.: US PP31,613 P2
(45) Date of Patent: Mar. 31, 2020

(54) ***MANDEVILLA* PLANT NAMED 'INMANBURG'**

(50) Latin Name: *Mandevilla sanderi*
Varietal Denomination: Inmanburg

(71) Applicant: Birgit Hofmann, Rudesheim am Rhein (DE)

(72) Inventor: Birgit Hofmann, Rudesheim am Rhein (DE)

(73) Assignee: Innovaplant Zierpflanzen GmbH & Co. KG, Gensingen (DE)

( * ) Notice: Subject to any disclaimer, the term of this patent is extended or adjusted under 35 U.S.C. 154(b) by 0 days.

(21) Appl. No.: 16/350,759

(22) Filed: Dec. 31, 2018

(51) Int. Cl.
*A01H 5/02* (2018.01)
*A01H 6/08* (2018.01)

(52) U.S. Cl.
USPC ..... Plt./232

(58) Field of Classification Search
USPC ..... Plt./232
See application file for complete search history.

*Primary Examiner* — Susan McCormick Ewoldt
(74) *Attorney, Agent, or Firm* — C. A. Whealy

(57) ABSTRACT

A new and distinct cultivar of *Mandevilla* plant named 'Inmanburg', characterized by its upright and vining plant habit; moderately vigorous growth habit; freely branching habit; moderately glossy dark green-colored leaves; freely flowering habit; dark red to greyed purple-colored flowers with greyed orange-colored centers; and relative tolerance to low temperatures.

2 Drawing Sheets

Botanical designation: *Mandevilla sanderi*.
Cultivar denomination: 'INMANBURG'.

BACKGROUND OF THE INVENTION

The present invention relates to a new and distinct cultivar of *Mandevilla* plant, botanically known as *Mandevilla sanderi* and hereinafter referred to by the name 'Inmanburg'.

The new *Mandevilla* plant is a product of a planned breeding program conducted by the Inventor in Johannesburg, South Africa and Heidesheim, Germany. The objective of the breeding program is to create new freely branching *Mandevilla* plants that flower freely and have attractive flowers that resist fading and sun scald.

The new *Mandevilla* plant originated from a cross-pollination conducted by the Inventor in Johannesburg, South Africa in January, 2014 of a proprietary selection of *Mandevilla sanderi* identified as code number D11-2149-1, not patented, as the female, or seed parent with a proprietary selection of *Mandevilla sanderi* identified as code number D11-2065-2, not patented, as the male, or pollen, parent. The new *Mandevilla* plant was discovered and selected by the Inventor as a single flowering plant from within the progeny of the stated cross-pollination in a controlled greenhouse environment in Heidesheim, Germany in June, 2015.

Asexual reproduction of the new *Mandevilla* plant by vegetative cuttings in a controlled greenhouse environment in Heidesheim, Germany since August, 2015 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Inmanburg'. These characteristics in combination distinguish 'Inmanburg' as a new and distinct *Mandevilla* plant:

1. Upright and vining plant habit.
2. Moderately vigorous growth habit.
3. Freely branching habit.
4. Moderately glossy dark green-colored leaves.
5. Freely flowering habit.
6. Dark red to greyed purple-colored flowers with greyed orange-colored centers.
7. Relatively tolerant to low temperatures.

Plants of the new *Mandevilla* can be compared to plants of the female parent selection. Plants of the new *Mandevilla* differ primarily from plants of the female parent selection in the following characteristics:

1. Plants of the new *Mandevilla* are more freely branching than plants of the female parent selection.
2. Plants of the new *Mandevilla* have smoother flowers than plants of the female parent selection.
3. Plants of the new *Mandevilla* have dark red to greyed purple-colored flowers with greyed orange-colored centers whereas plants of the female parent selection have dark red-colored flowers.

Plants of the new *Mandevilla* can be compared to plants of the male parent selection. Plants of the new *Mandevilla* differ primarily from plants of the male parent selection in the following characteristics:

1. Plants of the new *Mandevilla* are smoother leaves than plants of the male parent selection.
2. Plants of the new *Mandevilla* have dark red to greyed purple-colored flowers with greyed orange-colored centers whereas plants of the male parent selection have dark red-colored flowers.

Plants of the new *Mandevilla* can also be compared to plants of *Mandevilla* x *amabilis* 'Sunparacore', disclosed in U.S. Plant Pat. No. 23,959. In side-by-side comparisons plants of the new *Mandevilla* differ primarily from plants 'Sunparacore' in the following characteristics:

1. Plants of the new *Mandevilla* are more freely branching than plants of 'Sunparacore'.
2. Plants of the new *Mandevilla* have larger and more open flowers than plants of 'Sunparacore'.
3. Flowers of plants of the new *Mandevilla* are resistant sun scald whereas flowers of plants of 'Sunparacore' are not resistant to sun scald.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet comprises a side perspective view of a typical flowering plant of 'Inmanburg' grown in a container.

The photograph on the second sheet is a close-up view of a typical flowering plant of 'Inmanburg'.

DETAILED BOTANICAL DESCRIPTION

The aforementioned photographs and following observations, measurements and values describe plants grown during the spring and summer in 11-cm containers with wooden support frames in a glass-covered greenhouse in Heidesheim, Germany and under cultural practices typical of commercial *Mandevilla* production. During the production of the plants, day temperatures ranged from 20° C. to 40° C. and night temperatures ranged from 15° C. to 25° C. Plants were four months old when the photographs and description were taken. In the following description, color references are made to The Royal Horticultural Society Colour Chart, 2015 Edition, except where general terms of ordinary dictionary significance are used.

Botanical classification: *Mandevilla sanderi* 'Inmanburg'.

Parentage:

*Female, or seed, parent*.—Proprietary selection of *Mandevilla sanderi* identified as code number D11-2149-1.

*Male, or pollen, parent*.—Proprietary selection of *Mandevilla sanderi* identified as code number D11-2065-2.

Propagation:

*Type*.—By vegetative cuttings.

*Time to initiate roots, summer*.—About three weeks at temperatures ranging from 20° C. to 35° C.

*Time to initiate roots, winter*.—About three weeks at temperatures ranging from 20° C. to 25° C.

*Time to produce a rooted young plant, summer*.—About 20 to 25 days at temperatures ranging from 20° C. to 35° C.

*Time to produce a rooted young plant, winter*.—About 25 to 30 days at temperatures ranging from 20° C. to 25° C.

*Root description*.—Thick, fleshy; typically white in color, actual color of the roots is dependent on substrate composition, water quality, fertilizers, substrate temperature and physiological age of roots.

*Rooting habit*.—Low branching; medium density.

Plant description:

*Plant and growth habit*.—Upright and vining plant habit; roughly broadly obovate in overall shape; moderately vigorous growth habit and moderate growth rate.

*Plant height, soil level to top of foliar plane*.—About 30.7 cm.

*Plant height, soil level to top of floral plane*.—About 20.4 cm.

*Plant diameter* (*spread*).—About 31.3 cm.

*Lateral branch description*.—Branching habit: Freely branching habit, primary lateral branches each with about five secondary lateral branches. Length: About 28.2 cm. Diameter: About 2 mm. Internode length: About 3.8 cm. Aspect: Primary lateral branches, about 10° from vertical; secondary lateral branches, about 30° from primary branch axis. Strength: Strong. Texture and luster: Smooth, glabrous; glossy; becoming woody with development. Color, developing: Close to 144A. Color, developed: Close to 144A; when woody, close to N199A.

Leaf description:

*Arrangement*.—Opposite, simple.

*Length*.—About 7.9 cm.

*Width*.—About 3.8 cm.

*Shape*.—Elliptic to obovate.

*Apex*.—Apiculate to acute.

*Base*.—Truncate to obtuse.

*Margin*.—Entire; occasionally slightly undulate.

*Texture and luster, upper surface*.—Smooth, glabrous; moderately coriaceous; moderately glossy.

*Texture and luster, lower surface*.—Smooth, glabrous; moderately coriaceous; slightly glossy.

*Venation pattern*.—Pinnate.

*Color*.—Developing leaves, upper surface: Slightly darker than 147A. Developing leaves, lower surface: Close to N199B. Full expanded leaves, upper surface: Darker than between 139A and 147A; venation, close to 146A. Fully expanded leaves, lower surface: Close to 147B; venation, close to 144C.

*Petioles*.—Length: About 1.2 cm. Diameter: About 2 mm by 2 mm. Strength: Moderately strong. Texture and luster, upper and lower surfaces: Smooth, glabrous; moderately glossy. Color, upper surface: Close to 152B. Color, lower surface: Close to 145A.

Flower description:

*Flower type and flowering habit*.—Single salverform flowers arranged singly or in axillary cymes; flowers face outwardly to somewhat upright; freely flowering habit with about two flowers per inflorescence and about ten flower buds and open flowers per plant.

*Natural flowering season*.—Plants flower continuously from spring into the autumn in Germany; plants begin flowering about ten weeks after propagation.

*Flower longevity on the plant*.—Individual flowers last about ten days; flowers not persistent.

*Fragrance*.—None detected.

*Inflorescence height*.—About 7.9 cm.

*Inflorescence diameter*.—About 8.5 cm.

*Flower buds*.—Length: About 5.9 cm. Diameter: About 9 mm. Shape: Narrowly oblanceolate. Texture and luster: Smooth, glabrous; slightly glossy. Color: Distally, close to 53A; proximally, close to 53B; at the base, close to 145C and 145A.

*Flowers*.—Appearance: Flared trumpet, corolla fused and five-parted. Diameter: About 5.7 cm. Depth (length): About 6.7 cm. Throat diameter: About 1.3 cm. Tube length: About 5.1 cm. Tube diameter: Proximally, about 4 mm; distally, about 1.5 cm.

*Corolla*.—Quantity and arrangement: Five petals arranged in a single whorl; lower 62.5% portion of the petals are fused into a funnelform tube. Petal length: About 8.1 cm. Petal width: About 2 cm. Petal shape and appearance: Roughly spatulate. Petal apex: Apiculate. Petal margin: Entire; moderately undulate. Petal texture and luster, upper surface: Smooth, glabrous; very velvety; matte. Petal texture and luster, lower surface: Smooth, glabrous; slightly velvety; moderately glossy. Throat texture: Smooth, glabrous; very velvety. Tube texture: Smooth, glabrous; slightly velvety. Color: Petal, when opening, upper surface: Close to between 53A and 187B; fading towards the throat to close to 46A; at the throat, close to 53A. Petal, when opening, lower surface: Close to 53A. Petal, fully opened, upper surface: Close to between 53A and 187B; fading towards the throat to close to 46A; at the throat, close to 54B; venation, similar to lamina; with development, color becoming closer to 187B to 187C. Petal, fully opened, lower surface: Close to 53A; venation, similar to lamina; with development, color becoming closer to 1870 to 187D. Throat: Close to N163A; proximally, close to 145B; venation, similar to lamina. Tube: Close to 53A to 53B; proximally, close to 145C and 145A; venation, similar to lamina.

*Calyx*.—Quantity and arrangement: Five sepals arranged in a single whorl. Calyx length: About 7 mm. Calyx diameter: About 7 mm. Sepal length: About 6 mm. Sepal width: About 2 mm. Sepal shape: Lanceolate. Sepal apex: Narrowly acuminate. Sepal base: Broadly cuneate. Sepal margin: Entire. Sepal texture and luster, upper and lower surfaces: Smooth, glabrous; moderately glossy. Sepal color: When developing, upper and lower surfaces: Close to 145B; towards the base, close to 145A. Fully developed, upper and lower surfaces: Close to 145B; towards the base, close to 145A.

*Peduncles*.—Length: About 5.2 cm. Diameter: About 1.5 mm. Strength: Strong. Aspect: About 20° from lateral branch axis. Texture and luster: Smooth, glabrous; glossy. Color: Close to 143B.

*Pedicels*.—Length: About 1.4 cm. Diameter: About 2 mm. Strength: Strong. Aspect: About 10° to 30° from peduncle axis. Texture and luster: Smooth, glabrous; moderately glossy. Color: Close to 144A.

*Reproductive organs*.—Stamens: Quantity and arrangement: Typically five; basifixed; anthers connivent. Filament length: About 1.5 mm. Filament color: Close to 151D. Anther shape: Narrowly oblong. Anther size: About 1 cm by 1.5 mm. Anther color: Close to 160C. Pollen amount: None observed. Pistils: Quantity: Typically one. Pistil length: About 2.3 cm. Style length: About 2 cm. Style color: Close to 145C. Stigma diameter: About 2 mm. Stigma shape: Club-shaped, pointed. Stigma color: Close to 146D. Ovary color: Close to 144B.

*Seeds and fruits*.—To date, seed and fruit production have not been observed on plants of the new *Mandevilla*.

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate temperatures ranging from about 5° C. to about 40° C. and to be suitable for USDA Hardiness Zones 9 to 13.

It is claimed:

1. A new and distinct *Mandevilla* plant named 'Inmanburg' as illustrated and described.

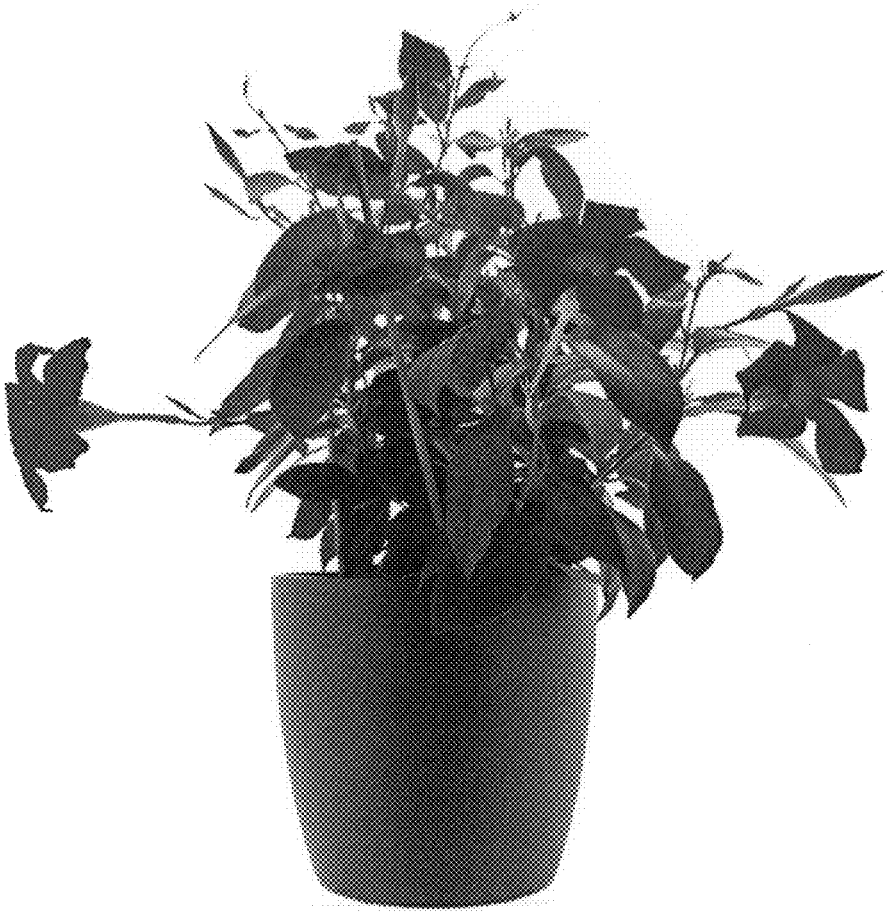

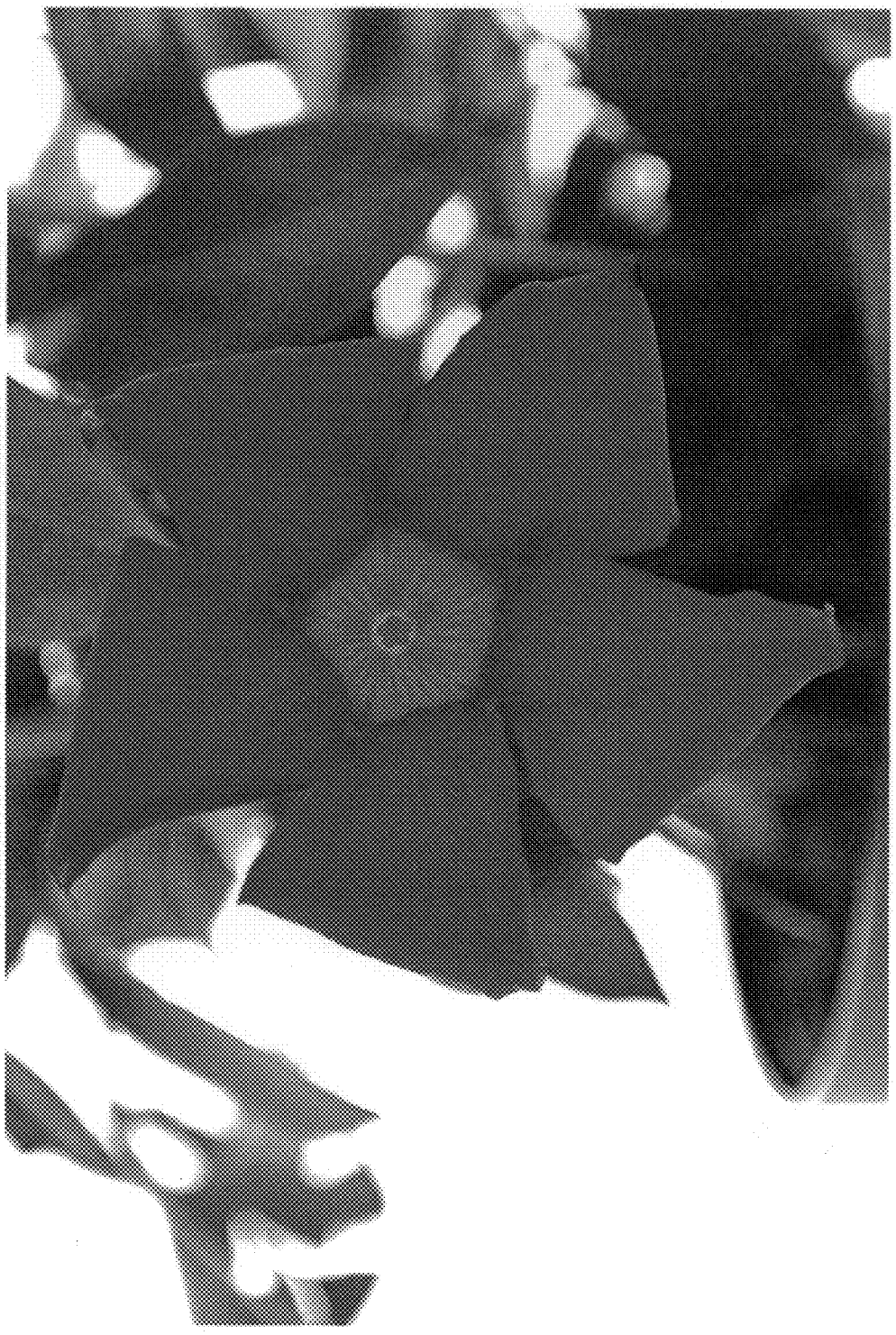

* * * * *